(12) United States Patent
Nazarifar et al.

(10) Patent No.: US 7,326,183 B2
(45) Date of Patent: Feb. 5, 2008

(54) INTRAOCULAR PRESSURE CONTROL

(75) Inventors: Nader Nazarifar, Laguna Niguel, CA (US); Frederick Reed, Cypress, CA (US); John C. Huculak, Mission Viejo, CA (US); Roger Thomas, Tustin, CA (US)

(73) Assignee: Alcon, Inc., Hunenberg (CH)

( * ) Notice: Subject to any disclaimer, the term of this patent is extended or adjusted under 35 U.S.C. 154(b) by 345 days.

(21) Appl. No.: 11/237,503

(22) Filed: Sep. 28, 2005

(65) Prior Publication Data
US 2007/0083150 A1 Apr. 12, 2007

(51) Int. Cl.
*A61M 1/00* (2006.01)
*A61M 31/00* (2006.01)
*A61M 5/00* (2006.01)

(52) U.S. Cl. .................. 604/30; 604/505; 604/246; 604/65

(58) Field of Classification Search ............ 604/30–35, 604/66, 67, 80, 82, 85, 118, 131, 132, 147, 604/151, 153, 245, 246, 249
See application file for complete search history.

(56) References Cited

U.S. PATENT DOCUMENTS

| | | | |
|---|---|---|---|
| 4,475,904 A | 10/1984 | Wang | |
| 4,713,051 A | 12/1987 | Steppe et al. | |
| 4,750,643 A | 6/1988 | Wortrich | |
| 4,758,238 A | 7/1988 | Sundblom et al. | |
| 4,813,927 A | 3/1989 | Morris et al. | |
| 4,832,685 A | 5/1989 | Haines | |
| 4,846,800 A * | 7/1989 | Ouriel et al. | 604/6.15 |
| 4,900,301 A | 2/1990 | Morris et al. | |
| 4,909,780 A * | 3/1990 | Ouriel et al. | 604/6.15 |
| 4,935,005 A | 6/1990 | Haines | |
| 4,963,131 A | 10/1990 | Wortrich | |
| 5,032,111 A | 7/1991 | Morris et al. | |
| 5,041,096 A | 8/1991 | Beuchat et al. | |
| 5,047,009 A | 9/1991 | Morris et al. | |
| 5,098,037 A | 3/1992 | Leffel et al. | |
| 5,106,366 A | 4/1992 | Steppe | |
| 5,163,900 A | 11/1992 | Wortrich | |
| 5,267,956 A | 12/1993 | Beuchat | |
| 5,282,787 A | 2/1994 | Wortrich | |
| D352,106 S | 11/1994 | Fanney et al. | |
| 5,364,342 A | 11/1994 | Beuchat et al. | |
| 5,499,969 A | 3/1996 | Beuchat et al. | |
| 5,563,584 A * | 10/1996 | Rader et al. | 340/618 |
| D375,553 S | 11/1996 | Creed et al. | |
| 5,582,601 A | 12/1996 | Wortrich et al. | |
| 5,588,815 A | 12/1996 | Zaleski, II | |
| 5,620,312 A | 4/1997 | Hyman et al. | |
| 5,630,798 A * | 5/1997 | Beiser et al. | 604/66 |
| D380,550 S | 7/1997 | Dennewill et al. | |
| 5,643,203 A | 7/1997 | Beiser et al. | |

(Continued)

FOREIGN PATENT DOCUMENTS

CA 1068572 12/1979

(Continued)

*Primary Examiner*—Samchuan C. Yao
*Assistant Examiner*—William Carpenter
(74) *Attorney, Agent, or Firm*—W. David Lee

(57) ABSTRACT

An improved method of controlling intraocular pressure with a microsurgical system using measured flow rate and a dual infusion chamber.

6 Claims, 2 Drawing Sheets

U.S. PATENT DOCUMENTS

| | | |
|---|---|---|
| 5,676,530 A | 10/1997 | Nazarifar |
| 5,676,650 A | 10/1997 | Grieshaber et al. |
| 5,700,240 A | 12/1997 | Barwick, Jr. et al. |
| 5,747,824 A | 5/1998 | Jung et al. |
| 5,776,104 A * | 7/1998 | Guignard et al. ............ 604/132 |
| 5,800,396 A | 9/1998 | Fanney et al. |
| 5,865,764 A | 2/1999 | Moorhead |
| 5,897,524 A | 4/1999 | Wortrich et al. |
| 5,899,674 A | 5/1999 | Jung et al. |
| 6,059,544 A | 5/2000 | Jung et al. |
| 6,261,283 B1 | 7/2001 | Morgan et al. |
| 6,293,926 B1 | 9/2001 | Sorensen et al. |
| 6,485,454 B1 * | 11/2002 | Yueh ........................... 604/80 |
| 6,491,661 B1 * | 12/2002 | Boukhny et al. ............. 604/67 |
| 6,561,999 B1 | 5/2003 | Nazarifar et al. |
| 6,572,349 B2 | 6/2003 | Sorensen et al. |
| 6,579,255 B2 | 6/2003 | Kadziauskas et al. |
| 6,632,214 B2 | 10/2003 | Morgan et al. |
| 6,740,074 B2 | 5/2004 | Morgan et al. |
| 6,824,525 B2 | 11/2004 | Nazarifar et al. |
| 6,902,542 B2 | 6/2005 | Gordon |
| 6,962,488 B2 | 11/2005 | Davis et al. |
| 2002/0019607 A1 | 2/2002 | Bui |
| 2002/0033370 A1 | 3/2002 | Bainbridge et al. |
| 2003/0050619 A1 | 3/2003 | Mooijman et al. |
| 2003/0108429 A1 | 6/2003 | Angelini et al. |
| 2003/0225363 A1 | 12/2003 | Gordon et al. |
| 2004/0253129 A1 | 12/2004 | Sorensen |
| 2005/0065462 A1 | 3/2005 | Nazarifar et al. |

FOREIGN PATENT DOCUMENTS

| | | |
|---|---|---|
| CA | 1068574 | 12/1979 |
| DE | 19852574 A1 | 5/2000 |
| EP | 0776670 B1 | 9/2001 |
| EP | 1356835 A1 | 10/2003 |
| EP | 1612532 A1 | 1/2006 |
| WO | WO 03/047652 A1 | 6/2003 |
| WO | WO 03/047653 A1 | 6/2003 |
| WO | WO 03/047654 A1 | 6/2003 |

* cited by examiner

INTRAOCULAR PRESSURE CONTROL

FIELD OF THE INVENTION

The present invention generally pertains to microsurgical systems and more particularly to controlling intraocular pressure in ophthalmic surgery.

DESCRIPTION OF THE RELATED ART

During small incision surgery, and particularly during ophthalmic surgery, small probes are inserted into the operative site to cut, remove, or otherwise manipulate tissue. During these surgical procedures, fluid is typically infused into the eye, and the infusion fluid and tissue are aspirated from the surgical site.

Maintaining an optimum intraocular pressure during ophthalmic surgery is currently problematic. When no aspiration is occurring, the pressure in the eye becomes the pressure of the fluid being infused into the eye. This pressure is typically referred to as the "dead head pressure". However, when aspiration is applied, the intraocular pressure drops dramatically from the dead head pressure due to all the pressure losses in the aspiration circuit associated with aspiration flow. Therefore, ophthalmic surgeons currently tolerate higher than desired dead head pressures to compensate for occasions when aspiration would otherwise lower the intraocular pressure to soft-eye conditions. Clinically, such over-pressurizing of the eye is not ideal.

Accordingly, a need continues to exist for an improved method of controlling intraocular pressure during ophthalmic surgery.

SUMMARY OF THE INVENTION

In one aspect, the present invention is a method of controlling intraocular pressure with a microsurgical system. An infusion chamber containing an irrigating fluid is provided, and a desired intraocular pressure is selected. The infusion chamber is pressurized with a pressurized gas to provide irrigating fluid to a surgical device. A flow rate of the fluid within a fluid line fluidly coupled to the surgical device is measured. A signal corresponding to the measured flow rate is provided to a computer. A predicted intraocular pressure is calculated with the computer in response to the signal. A level of the pressurized gas is adjusted in response to a second signal from the computer to maintain the predicted intraocular pressure proximate the desired intraocular pressure.

In another aspect of the present invention, an infusion chamber is provided. The infusion chamber has a first chamber for holding irrigating fluid and a second chamber for holding irrigating fluid. The first chamber is not fluidly coupled to the second chamber. An irrigating fluid is provided from an infusion source to the first chamber and the second chamber. The irrigating fluid is provided to a surgical device from the first chamber during a microsurgical procedure, and this step is ended when the level of the irrigating fluid in the first chamber reaches a bottom limit. Upon such ending, the irrigating fluid is provided to the surgical device from the second chamber, and the first chamber is refilled with the irrigating fluid from the infusion source.

BRIEF DESCRIPTION OF THE DRAWINGS

For a more complete understanding of the present invention, and for further objects and advantages thereof, reference is made to the following description taken in conjunction with the accompanying drawings, in which.

DETAILED DESCRIPTION OF THE PREFERRED EMBODIMENTS

Figure 1:
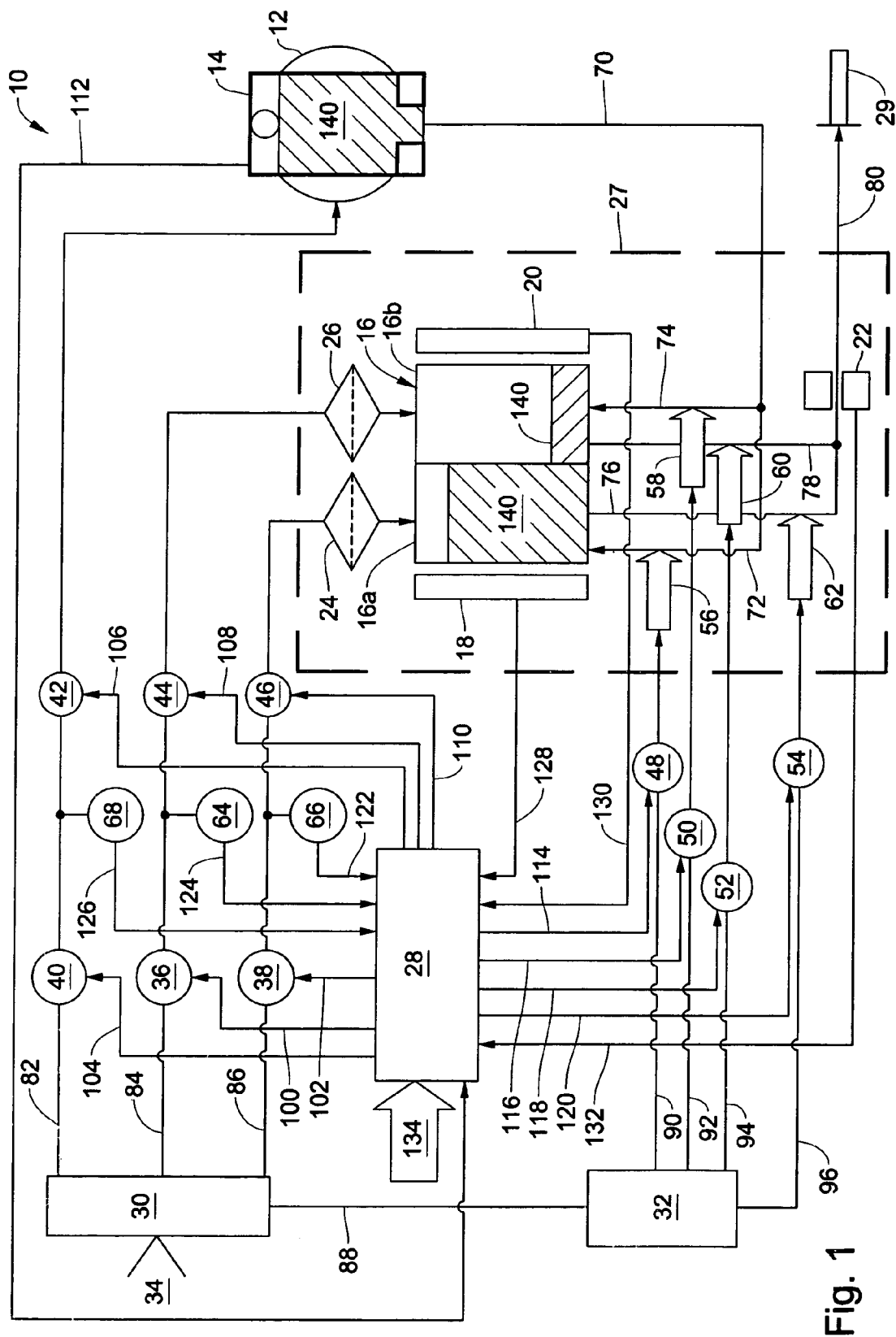
FIG. 1 is a schematic diagram illustrating infusion control in an ophthalmic microsurgical system.
Figure 2:
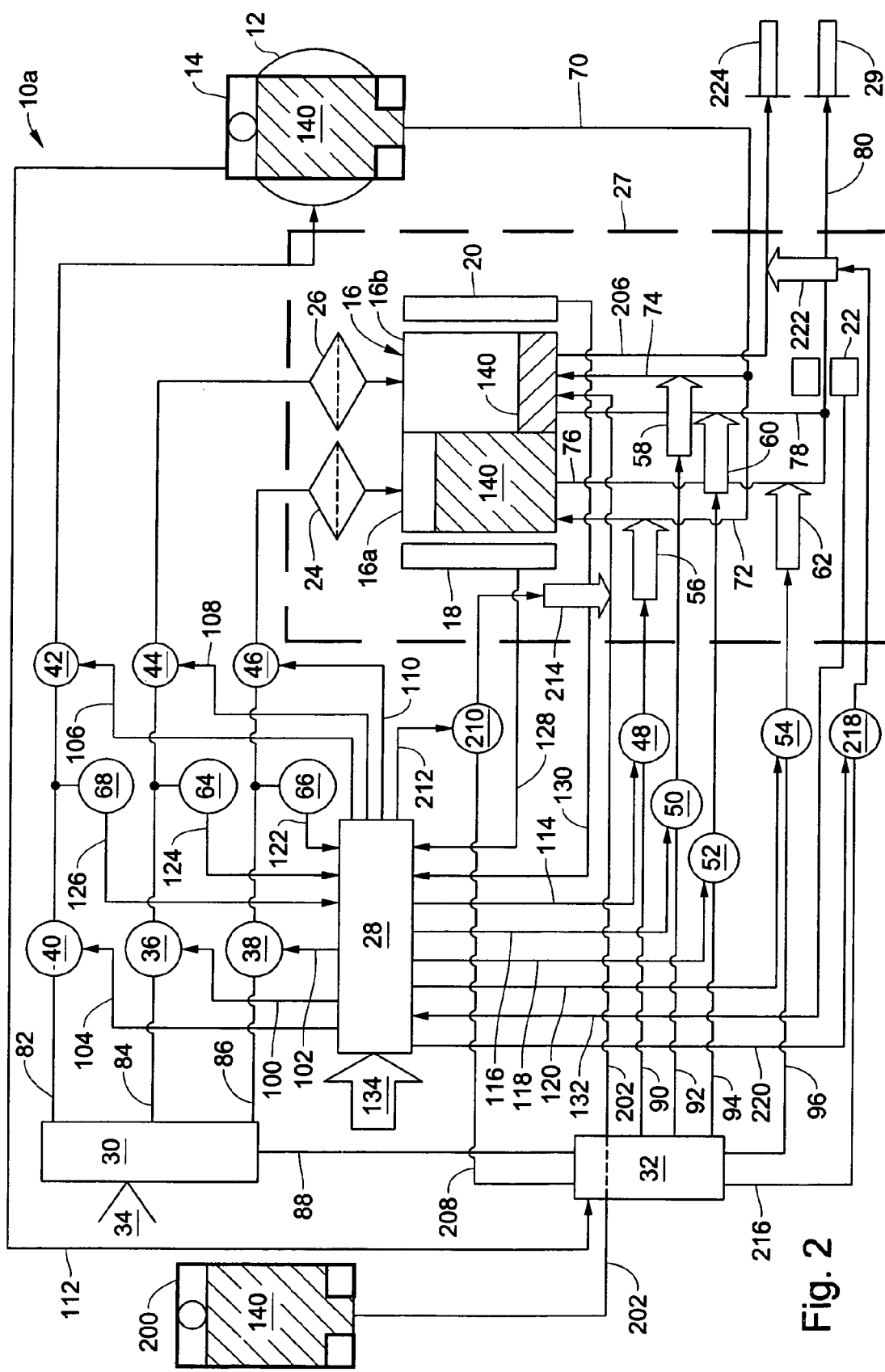
FIG. 2 is a schematic diagram illustrating infusion control and irrigation control in an ophthalmic microsurgical system.

The preferred embodiments of the present invention and their advantages are best understood by referring to FIGS. 1-2 of the drawings, like numerals being used for like and corresponding parts of the various drawings. As shown in FIG. 1, ophthalmic microsurgical system 10 includes a pressure cuff 12; an infusion source 14; a dual infusion chamber 16 having a chamber 16a and a chamber 16b; fluid level sensors 18 and 20; a flow sensor 22; filters 24 and 26; a surgical device 29; a computer or microprocessor 28; gas manifolds 30 and 32; a pressurized gas source 34; proportional solenoid valves 36, 38, and 40; "on/off" solenoid valves 42, 44, 46, 48, 50, 52, 54; actuators 56, 58, 60, and 62; and pressure transducers 64, 66, and 68. Dual infusion chamber 16; fluid level sensors 18 and 20; portions of infusion fluid lines 70, 72, 74, 76, 78, and 80; and portions of gas lines 84 and 86 are preferably disposed in a surgical cassette 27. Infusion source 14; dual infusion chamber 16; flow sensor 22; filters 24 and 26; and surgical device 29 are fluidly coupled via infusion fluid lines 70-80. Infusion source 14, dual infusion chamber 16, gas manifolds 30 and 32; pressurized gas source 34; and actuators 56, 58, 60, and 62 are fluidly coupled via gas lines 82, 84, 86, 88, 90, 92, 94, and 96. Infusion source 14; fluid level sensors 18-20; flow sensor 22; microprocessor 28; proportional solenoid valves 36-40; on/off solenoid valves 42-54; actuators 56-62; and pressure transducers 64-68 are electrically coupled via interfaces 100, 102, 104, 106, 108, 110, 112, 114, 116, 118, 120, 122, 124, 126, 128, 130, and 132.

Infusion source 14 is preferably a flexible infusion source. Fluid level sensors 18 and 20 may be any suitable device for measuring the level of fluid in infusion chambers 16a and 16b, respectively. Fluid level sensors 18 and 20 are preferably capable of measuring the level of fluid in infusion chambers 16a and 16b in a continuous manner. Flow sensor 22 may be any suitable device for measuring the flow rate of fluid within fluid line 80. Flow sensor 22 is preferably a non-invasive flow sensor. Filters 24 and 26 are hydrophobic micro-bacterial filters. A preferred filter is the Versapor® membrane filter (0.8 micron) available from Pall Corporation of East Hills, N.Y. Microprocessor 28 is capable of implementing feedback control, and preferably PID control. Surgical device 29 may be any suitable device for providing surgical irrigating fluid to the eye but is preferably an infusion cannula, an irrigation handpiece, or and irrigation/aspiration handpiece.

In operation, fluid lines 70, 72, and 74; chambers 16a and 16b; fluid lines 76, 78, and 80; and surgical device 29 are all primed with a surgical irrigating fluid 140 by pressurizing infusion source 14. Surgical irrigating fluid 140 may be any surgical irrigating fluid suitable for ophthalmic use, such as, by way of example, BSS PLUS® intraocular irrigating solution available from Alcon Laboratories, Inc.

The pressurizing of infusion source 14 is preferably performed by pressure cuff 12. More specifically, microprocessor 28 sends a control signal to open solenoid valve 42 via interface 106 and to close solenoid valves 44 and 46 via interfaces 108 and 110, respectively. Microprocessor 28 also sends a control signal to open proportional solenoid valve 40 via interface 104 so that manifold 30 supplies the appropriate amount of pressurized air to actuate pressure cuff 12. Pressure transducer 68 senses the pressure within gas line 82 and provides a corresponding signal to microprocessor 28 via interface 126. Solenoid valves 48-54 are initially open so that manifold 32 provides pressurized air to actuate actuators 56-62 to close fluid lines 72-78. Microprocessor 28 sends control signals to close solenoid valves 48-54 via interfaces 114-120. The closing of solenoid valves 48-54 actuates actuators 56-62 to open fluid lines 72-78. After all chambers and fluid lines are primed, microprocessor 28 closes actuators 56-62 and thus fluid lines 72-78. Alternatively, the pressuring of infusion source 14 may be performed solely via gravity.

After priming, a user then provides a desired intraocular pressure to microprocessor 28 via an input 134. Input 134 may be any suitable input device but is preferably a touch screen display or physical knob. Chamber 16*b* is preferably the initial active infusion chamber. Microprocessor 28 sends appropriate control signals to open solenoid valve 44 and to open proportional solenoid valve 36 (via interface 100) to provide an appropriate level of pressurized air to chamber 16*b*. Pressure transducer 64 senses the pressure within gas line 84 and provides a corresponding signal to microprocessor 28 via interface 124. Microprocessor 28 also sends an appropriate control signal to open actuator 60 and thus fluid line 78. Chamber 16*b* supplies pressurized fluid 140 to the eye via fluid lines 78 and 80 and surgical device 29. Flow sensor 22 measures the flow rate of fluid 140 and provides a corresponding signal to microprocessor 28 via interface 132. Microprocessor 28 calculates a predicted intraocular pressure using the signal from flow sensor 22 and empirically determined impedance information of microsurgical system 10. Microprocessor 28 then sends an appropriate feedback control signal to proportional solenoid valve 36 to maintain the predicted intraocular pressure at or near the desired intraocular pressure during all portions of the surgery.

Fluid level sensor 20 continuously monitors the decrease in the level of fluid 140 in chamber 16*b* during surgery and provides a corresponding signal to microprocessor 28 via interface 130. Microprocessor 28 performs adjustments to the air pressure provided to chamber 16*b* to accommodate for the difference in fluid head height as the level of fluid 140 decreases. When the level of fluid 140 in chamber 16*b* reaches a bottom limit level, microprocessor 28 closes solenoid valve 44 and actuator 60 and opens solenoid valve 46 and actuators 58 and 62. Chamber 16*a* is now the active infusion chamber. Microprocessor 28 sends an appropriate control signal to proportional solenoid valve 38 via interface 102 to provide an appropriate level of pressurized air to chamber 16*a*. Pressure transducer 66 senses the pressure within gas line 86 and provides a corresponding signal to microprocessor 28 via interface 122. Chamber 16*a* supplies pressurized fluid 140 to the eye via fluid lines 76 and 80 and surgical device 29. Flow sensor 22 measures the flow rate of fluid 140 and provides a corresponding signal to microprocessor 28 via interface 132. Microprocessor 28 calculates the predicted intraocular pressure as described above and the sends an appropriate feedback signal to proportional solenoid valve 38 to maintain the predicted intraocular pressure at or near the desired intraocular pressure during all portions of the surgery. Microprocessor 28 closes actuator 58 and fluid line 74 once chamber 16*b* is refilled with fluid 140.

Fluid level sensor 18 continuously monitors the decrease in the level of fluid 140 in chamber 16*a* during surgery and provides a corresponding signal to microprocessor 28 via interface 128. Microprocessor 28 performs adjustments to the air pressure provided to chamber 16*a* to accommodate for the difference in fluid head height as the level of fluid 140 decreases. When the level of fluid 140 in chamber 16*a* reaches a bottom limit level, microprocessor 28 switches chamber 16*b* to active infusion, makes chamber 16*a* inactive, and refills chamber 16*a* with fluid 140 via fluid line 72. This cycling between chambers 16*b* and 16*a* continues throughout the surgery.

Infusion source 14 is preferably monitored via a fluid level sensor (not shown) capable of providing a signal to microprocessor 28 via interface 112 when source 14 reaches a near empty limit. Chambers 16*a* and 16*b* also preferably each have a volume that enable infusion source 14 to be exchanged, when near empty, without interrupting the surgical procedure. More specifically, chambers 16*a* and 16*b* preferably each have a volume of about 30 cc. Such volume allows about two minutes for a near empty infusion source 14 to be exchanged during conditions of maximum flow (e.g. core vitrectomy). In addition, once infusion source 14 is exchanged, all air bubbles within fluid lines 70, 72, and 74 will be automatically "scrubbed out" as the inactive chamber 16*a* or 16*b* refills, without the need for re-priming.

In the case of failure of either of chambers 16*a* or 16*b*, microprocessor 28 can preferably continue surgery with only one active chamber. In the case of failure of both chambers 16*a* and 16*b*, microprocessor 28 can preferably continue surgery using only infusion source 14.

FIG. 2 shows a modified ophthalmic microsurgical system 10*a*. Microsurgical system 10*a* is similar to microsurgical system 10 except that it has an irrigation system in addition to the infusion system described above for system 10. More specifically, system 10*a* is identical to system 10 except that system 10*a* also includes an irrigation source 200; fluid lines 202 and 206; gas lines 208 and 216; solenoid valves 210 and 218; actuators 214 and 222; electrical interfaces 212 and 220; and a surgical device 224. As shown in FIG. 2, irrigation source 200 is pressurized solely by gravity. As will be appreciated by one of ordinary skill in the art, microsurgical system 10*a* allows surgical irrigating fluid 140 to be delivered to surgical device 29 via fluid line 80 (infusion), and surgical irrigating fluid 140 to be delivered to surgical device 224 via fluid line 206 (irrigation), independently. Microprocessor 28 can calculate flow information for fluid 140 within fluid line 206 by continuously monitoring the volumetric change of fluid inside chamber 16*b*, as indicated by fluid sensor 20.

From the above, it may be appreciated that the present invention provides an improved method of controlling intraocular pressure with a microsurgical system. The present invention is illustrated herein by example, and various modifications may be made by a person of ordinary skill in the art. For example, while the present invention is described above relative to controlling intraocular pressure in an ophthalmic microsurgical system, it is also applicable to controlling pressure within the operative tissue during other types of microsurgery.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of controlling intraocular pressure with a microsurgical system, comprising the steps of:
   providing an infusion chamber, said infusion chamber having a first chamber for holding irrigating fluid and a second chamber for holding irrigating fluid, said first chamber not fluidly coupled to said second chamber;
   providing an irrigating fluid from an infusion source to said first chamber and said second chamber wherein said infusion source is fluidly coupled to said first chamber and said second chamber during priming of said chambers;
   providing said irrigating fluid to a surgical device from said first chamber during a microsurgical procedure;
   ending said third providing step when said level of said irrigating fluid in said first chamber reaches a bottom limit;
   upon said ending step, providing said irrigating fluid to said surgical device from said second chamber; and
   refilling said first chamber with said irrigating fluid from said infusion source during said fourth providing step.

2. The method of claim 1 further comprising the steps of:
   ending said fourth providing step when said level of said irrigating fluid in said second chamber reaches a second bottom limit;
   re-initiating said third providing step; and
   refilling said second chamber with said irrigating fluid from said infusion source during said re-initiating of said third providing step.

3. The method of claim 1 further comprising the steps of:
   detecting when said infusion source reaches a third bottom level limit; and
   exchanging said infusion source without interrupting one of either of said third [providing] step or said fourth providing step.

4. The method of claim 1 wherein said ending step comprises detecting said bottom limit with a fluid level sensor.

5. The method of claim 2 wherein said ending step comprises detecting said second bottom limit with a fluid level sensor.

6. The method of claim 1 further comprising the steps of:
   providing said irrigating fluid from an irrigation source to one of said first chamber or said second chamber, said irrigation source not fluidly coupled to said infusion source; and
   providing said irrigating fluid to a second surgical device from said one of said first chamber or said second chamber.

* * * * *

UNITED STATES PATENT AND TRADEMARK OFFICE
CERTIFICATE OF CORRECTION

PATENT NO. : 7,326,183 B2  Page 1 of 1
APPLICATION NO. : 11/237503
DATED : February 5, 2008
INVENTOR(S) : Nazarifar et al.

It is certified that error appears in the above-identified patent and that said Letters Patent is hereby corrected as shown below:

Col. 6, ln. 8, delete "[providing]" and insert --providing--.

Signed and Sealed this

Twenty-second Day of July, 2008

JON W. DUDAS
*Director of the United States Patent and Trademark Office*